(12) United States Patent
Pettegrew et al.

(10) Patent No.: US 8,329,142 B2
(45) Date of Patent: Dec. 11, 2012

(54) COMPOUNDS, COMPOSITIONS AND METHODS FOR MEDICAL IMAGING OF PARKINSON'S DISEASE

(76) Inventors: Jay W. Pettegrew, Pittsburgh, PA (US); Richard J. McClure, Pittsburgh, PA (US); Kanagasabai Panchalingam, Monroeville, PA (US)

( * ) Notice: Subject to any disclaimer, the term of this patent is extended or adjusted under 35 U.S.C. 154(b) by 1061 days.

(21) Appl. No.: 12/178,281

(22) Filed: Jul. 23, 2008

(65) Prior Publication Data
US 2008/0292557 A1   Nov. 27, 2008

Related U.S. Application Data

(63) Continuation-in-part of application No. 10/854,894, filed on May 27, 2004, now Pat. No. 7,815,894.

(60) Provisional application No. 60/474,182, filed on May 29, 2003.

(51) Int. Cl.
*A61K 51/00* (2006.01)
*A61M 36/14* (2006.01)

(52) U.S. Cl. .......... 424/1.89; 424/1.11; 424/1.65; 424/1.81; 424/1.85; 424/9.1

(58) Field of Classification Search .......... 424/1.11, 424/1.65, 1.73, 1.77, 1.81, 1.85, 1.89, 9.1, 424/9.2, 9.3, 9.4, 9.5, 9.6, 9.7, 9.8
See application file for complete search history.

(56) References Cited

U.S. PATENT DOCUMENTS 5,631,168 A * 5/1997 Growdon et al. .......... 436/71
7,815,894 B2 * 10/2010 Pettegrew et al. .......... 424/1.77

* cited by examiner

*Primary Examiner* — D L Jones
(74) *Attorney, Agent, or Firm* — Barbara E. Johnson, Esq.

(57) ABSTRACT

Compounds, compositions and methods for the detection and diagnosis of Parkinson's disease. Derivative lycerophosphocholine (GPC) compounds are used as a detection and diagnostic aid to measure progression of Parkinson's disease by detecting GPC binding to α-synuclein. Derivative CPG compounds including non-radioactive, paramagnetic, and radioactive derivatives of GPC are presented. These compounds possess similar binding properties to original GPC molecules and are useful in medical magnetic resonance imaging (MRI) and/or positron emission tomography (PET) applications. By employing these radiological techniques in conjunction with the compositions of the present invention, the detection, diagnosis and assessment of the progression of Parkinson's disease may be achieved.

2 Claims, 14 Drawing Sheets

AXIAL MRI SLICE OF THE BRAIN TO SHOW GLOBUS PALLIDUS AND PUTAMEN REGIONS WITH LEWY BODY DEPOSITS WHICH ARE COMPOSED OF AGGREGATED ALPHA-SYNUCLEIN FOR DETECTION AND DIAGNOSIS OF PARKINSON'S DISEASE

COMPOUNDS, COMPOSITIONS AND METHODS FOR MEDICAL IMAGING OF PARKINSON'S DISEASE

CROSS REFERENCES TO RELATED APPLICATIONS

This application is a Continuation-In-Part (CIP) of U.S. patent application Ser. No. 10/854,894 filed, May 27, 2004, that claims priority to U.S. Provisional Patent Application No. 60/474,182, filed on May 29, 2003, the contents of all of which are incorporated by reference.

FIELD OF THE INVENTION

The present invention relates to compounds, compositions and methods for synthesis and use adapted for medical imaging of the progression of neuropsychiatric disorders, generally, and of Parkinson's disease, specifically.

BACKGROUND OF THE INVENTION

The most common form of dementia among the elderly is Alzheimer's disease. Alzheimer's disease is a progressive, neurodegenerative disease characterized by memory loss, language deterioration, impaired visuospatial skills, poor judgment, indifferent attitude, but preserved motor function. At the neuroanatomical level, Alzheimer's disease is characterized by loss of synapses and neuronal cell death accompanied by the formation of extracellular senile plaques and intracellular neurofibrillary tangles.

The causes of Alzheimer's disease have been widely studied, but remain poorly understood. Nevertheless, the initial molecular events in Alzheimer's disease resulting in neuronal cell death are widely considered to involve senile plaques. The senile plaques in the diseased brain are irregular, approximately spherical, and are found commonly in the cerebral cortex and hippocampus of brains of Alzheimer's disease patients. A major component of the senile plaques is a form of amyloid peptide. The amyloid peptide that accumulates in the senile plaques notably contains β-pleated sheets, whereas the normal amyloid peptide contains α-helices and random coils.

The particular beta amyloid (Aβ) peptide that accumulates in senile plaques is a 39-43 amino acid degradation product of the naturally-occurring transmembrane protein amyloid precursor protein. Soluble a-helical or random coil conformations of Aβ peptides have little or no neurotoxicity. However, in vitro studies have established that the fibrillar β-pleated sheet conformation of Aβ is neurotoxic (See, e.g., Yankner et al., Science 1990; 250: 279-282, the contents of which are incorporated by reference). One of the significant questions in Alzheimer's disease research is, Why does Aβ peptide begin to form β-pleated sheets to such a large degree in Alzheimer's disease?

Membrane phospholipid changes in addition to abnormal Aβ formation have been reported in Alzheimer's disease. Research has demonstrated major alterations in membrane phospholipid metabolism in the brains of Alzheimer's disease patients, including changes in phospholipid composition (Pettegrew et al., Neurochem. Res. 2001; 26: 771-782, the contents of which are hereby incorporated by reference); changes in phospholipid metabolic enzymes (See, e.g., Kanfer et al., Neurochem. Res. 1993; 18: 331-334, the contents of which are incorporated herein by reference); and changes in the precursors and breakdown products of membrane phospholipids (See, e.g., Pettegrew et al., Brain Res. Bull. 2000, 53(4): 455-469, the contents of which are incorporated herein by reference). Changes in membrane phospholipid and high-energy phosphate metabolism have been demonstrated by in vivo $^{31}P$ magnetic resonance imaging in a pre-symptomatic individual 33 months prior to the diagnosis of possible incipient dementia and 46 months prior to the diagnosis of Alzheimer's disease dementia. Together, these data suggest a causal role of membrane phospholipid metabolic processes in the development of Alzheimer's disease.

Glycerophosphocholine ($C_8H_{20}PO_6N$, hereinafter abbreviated as GPC) is a normal membrane phospholipid breakdown product of phosphatidylcholine that is produced by the combined action of phospholipase A and lysophospholipase activity in all tissues, including brain. The normal levels of GPC in adult human brain are 1-2 mM and the levels are developmentally and aging regulated. The levels of GPC in brain naturally increase with age, but increase to a much greater degree in patients with Alzheimer's disease. The parallels between brain GPC levels and Alzheimer's disease raises the intriguing possibility that GPC plays a causal role in Alzheimer's disease.

In vitro studies were conducted to examine if GPC could affect the formation of Aβ peptide β-sheet deposits. The results of those studies showed that GPC enhanced Aβ(1-40) aggregation by over 400% (see, e.g., Klunk et al., J. Neurochem. 1997; 69: 266-272, the contents of which are incorporated herein by reference). Further studies demonstrated that GPC reduces the α-helical content of Aβ(1-40) by 15%, thus directly demonstrating that GPC is able to alter the conformation of Aβ peptides (See, e.g., Pettegrew et al., 2003 Abstract Viewer, Soc. Neurosci., Program No. 944.2, the contents of which are incorporated herein by reference). These results further support the idea that GPC may play a causal role in the development of Alzheimer's disease.

Computer-based molecular modeling studies have suggested a mechanism of action by which GPC stabilizes a β-turn in Aβ peptide. The molecular interaction of GPC with Aβ(1-28), which is known to determine the kinetics of Aβ aggregation, was studied by computer-based molecular mechanics and dynamics modeling (See, e.g., McClure et al., Soc. Neurosci. Abstr. 2001; 27, abstract 322.9, the contents of which are incorporated herein by reference). GPC was found to bind specifically to a site in the Aβ(1-28) peptide that forms a pocket comprised of three amino acids—namely Lys28, -Asp23, and -Lys16. Moreover, GPC binding to this peptide pocket promotes a transition β-turn conformation of the Aβ peptide. Introducing a β-turn in the Aβ peptide is critical and essential in order for Aβ peptide to form a β-sheet conformation which is the Aβ conformation which aggregates into senile plaques (FIG. 1). These data pointed to GPC as possibly playing a causal role in β-sheet aggregation of Aβ peptide.

To address the question of the specificity of GPC binding to Aβ peptides, protein structures deposited in the Protein Data Bank (PDB) were examined. In this molecular modeling approach, proteins were inspected for potential binding sites of GPC that resembled the binding site on Aβ peptides. Some 11,996 structures were compared and the top 117 matches were examined further to determine the matches that contained the correct sequence. Protein homology analysis further limited the results to five likely candidates. However, visual inspection of these protein structures did not reveal binding pockets similar to the proposed site for GPC. Based on this search and additional searches of the PDB database, it appears that the Lys28-Asp23-Lys16 motif that produces the proposed GPC binding site is unique to Aβ peptide structures.

Furthermore, the spatial orientation of the Lys28-Asp23-Lys16 residues found in Aβ also appears to be important. These observations suggest that the binding of GPC to Aβ is highly specific.

Since both GPC and Aβ interact with or are generated from the cellular lipid membrane, the manner in which these two molecular species might normally interact was investigated. Fluorescence spectroscopy studies were conducted on normal human erythrocytes and rat brain membranes and results from them confirmed that GPC and Aβ(1-40) interact within the natural environment of membrane phospholipids (See, e.g., Mandal et al., submitted to Neurochem. Res. 2004, the contents of which are incorporated herein by reference).

Previous research efforts have demonstrated that GPC can induce β turns in the Aβ peptide, which may then lead to the formation of extracellular β sheets. The β sheets may, in turn, promote the formation of aggregates of Aβ peptide in senile plaques in Alzheimer's disease, leading to loss of synapses and neuronal cell death. In Alzheimer's disease, brain concentrations of GPC have been shown to increase with age and prior to the expression of Alzheimer's disease symptoms.

However, there has been no suggestion or teaching in the prior art of how to employ these scientific observations in the treatment or diagnosis of Parkinson's disease.

There is also a long-standing need within the medical community for a diagnostic tool for assessing the pre-symptomatic onset of Parkinson's disease. Thus, it is desirable to provide compositions and methods that are useful for the pre-symptomatic measurement of in the development of Parkinson's disease.

SUMMARY OF THE INVENTION

In accordance with preferred embodiments of the present invention, some of the problems presently associated with the diagnosis Parkinson's disease are overcome.

Compounds, compositions and methods for the detection and diagnosis of Parkinson's disease. Derivative glycerophosphocholine (GPC) compounds are used as a detection and diagnostic aid to measure progression of Parkinson's disease by detecting GPC binding to α-synuclein. Derivative compounds including non-radioactive, paramagnetic, and radioactive derivatives of GPC are presented. These compounds possess similar binding properties to original GPC molecules and are useful in medical magnetic resonance imaging (MRI) and/or positron emission tomography (PET) applications. By employing these radiological techniques in conjunction with the compositions of the present invention, the detection, diagnosis and assessment of the progression of Parkinson's disease may be achieved.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein.

DETAILED DESCRIPTION THE INVENTION

Figure 1:
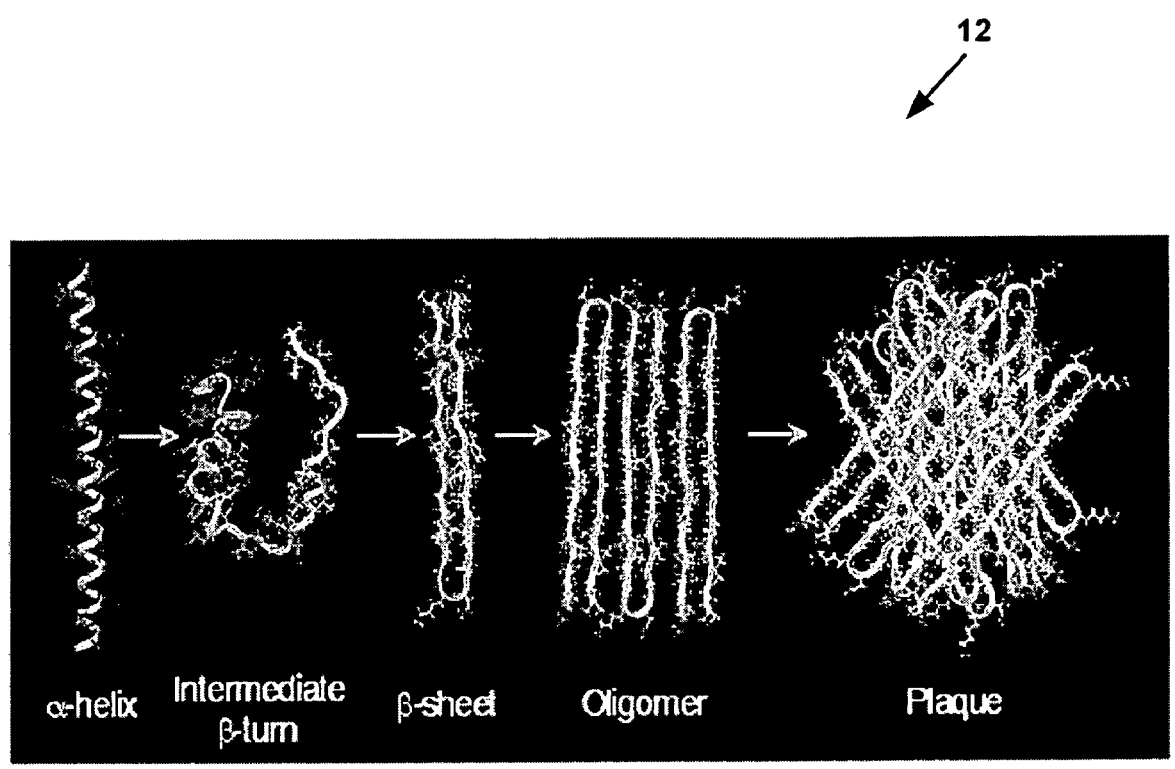
FIG. 1 is a molecular schematic diagram illustrating the formation of senile plaques from Aβ peptide.

FIG. 1 is a molecular schematic diagram 10 illustrating the formation of senile plaques from Aβ peptide. A β-turn is introduced into an Aβ peptide to form a β-sheet conformation which is the Aβ conformation which aggregates into senile plaques.

Figure 2:
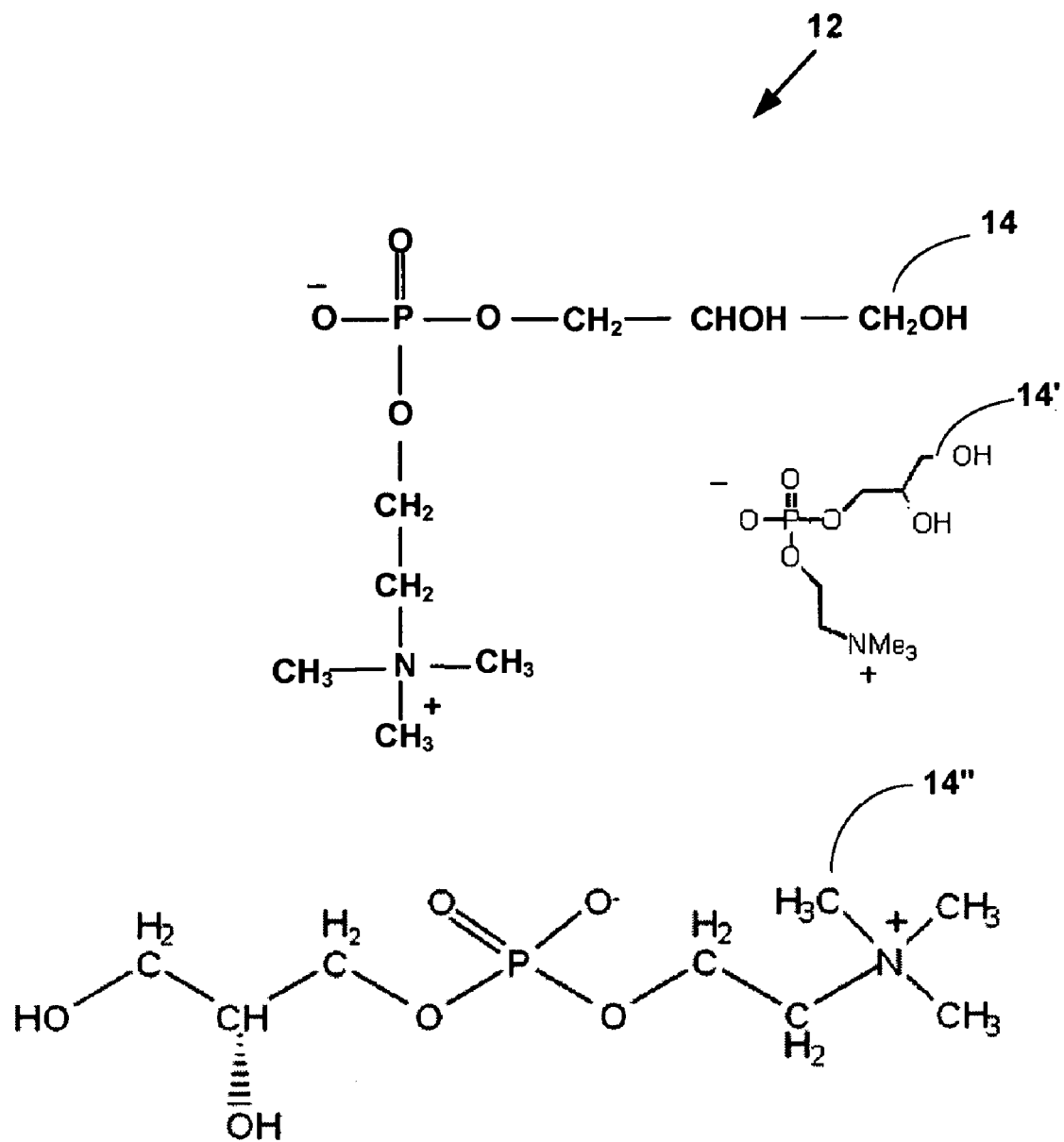
FIG. 2 is a block diagram illustrating a chemical formula for a glycerophosphocholine (GPC) molecule.

FIG. 2 is a block diagram 12 illustrating a chemical formula for glycerophosphocholine ($C_8H_{20}PO_6N$, hereinafter abbreviated as GPC) molecule 14 as shown in the below formula:

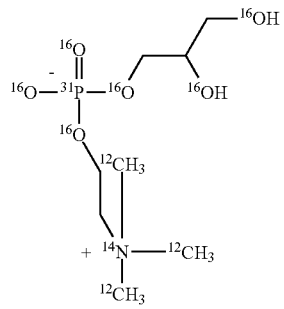

FIG. 2 also illustrates equivalent representations 14', 14" of the same GPC molecule 14. As is known in the medical arts, GPC specifically binds to Aβ peptides and can promote the formation of a β-turn in Aβ peptide which promotes β-sheet aggregates found in senile plaques. Therefore, GPC can be used for the non-invasive measurement of Aβ peptides containing β-turns in human and animal subjects. GPC molecules are capable of efficiently crossing the blood-brain barrier and subsequently specifically binding to Aβ peptides containing β-turns.

In one embodiment of the invention, GPC compounds are synthesized that include, but are not limited to, derivatives of GPC that are capable of being imaged via standard brain imaging techniques such as magnetic resonance imaging (MRI), positron emission tomography (PET) and other such medical imaging techniques known in the art. Such GPC compounds are used as a chemical means to diagnose Alzheimer's disease in humans.

As is known in the art, MRI is a diagnostic technique in which radio waves generated in a strong magnetic field are used to provide information about hydrogen atoms in different tissues within a human body. A computer uses this information to produce two and three dimensional images of the tissues in many different planes. For example, human tissues that are well-visualized using MRIs include soft tissues such as the brain and spinal cord, abdomen, and joints.

As is known in the art, PET is a type of nuclear medicine imaging in which very small amounts of radioactive materials are used to diagnose diseases. A radioactive tracer is injected into a vein, swallowed by mouth or inhaled as a gas and eventually collects in the area of a human body being examined, where it gives off energy in the form of gamma rays. This energy is detected by a PET scanner. These devices work together with a computer to measure the amount of radio active tracer absorbed by a body and to produce special pictures offering details on both the structure and function of organs and other internal body parts. PET scans measure important body functions, such as blood flow, oxygen use, and sugar metabolism, to help doctors evaluate how well organs and tissues are functioning.

Since it was known that GPC enters the brain following intra-venous (IV) and oral administration (See, e.g., Abbiatti et al., Eur. J. Drug Metab. Pharmacokinet. 1993; 18: 173-180, the contents of which are incorporated herein by reference), non-radioactive ($^{19}$F, $^{16}$O), paramagnetic ($^{17}$O) and radioactive ($^{15}$O, $^{13}$N, $^{11}$C, $^{18}$F) derivatives of GPC may be synthesized for use in MRI ($^{17}$O, $^{19}$F) and PET ($^{15}$O, $^{13}$N, $^{11}$C, $^{18}$F) imaging. The interaction between GPC and the Aβ peptide is governed by highly specific chemical and physical spacing and interactions between the two molecules. Therefore, the molecules of the present invention preferably do not contain large marker groups or fluorescent tags that are attached to GPC, as such hybrid molecules may disrupt the specific binding of GPC to Aβ peptides. Instead, the present invention uses molecules in which at least one of the atomic moieties of a normal GPC is replaced with a non-radioactive ($^{19}$F), paramagnetic ($^{17}$O), or radioactive ($^{15}$O, $^{13}$N, $^{11}$C, $^{18}$F) isotope of the same or physiochemically related moiety.

An $^{17}$O-containing derivative of GPC is one preferred embodiment of an imaging molecule within the context of the present invention. $^{17}$O is a stable isotope of oxygen that has a nuclear spin of 5/2. This isotope enhances proton ($^1$H) $T_2$ relaxation rates through its scalar-coupled interactions (See, e.g., Meiboom et al., J. Chem. Phys. 1957; 27: 1411-1412; Meiboom, J. Chem. Phys. 1961; 34: 375-388, the contents of which are incorporated herein by reference), thus making it useful in MRI imaging applications.

Figure 3:
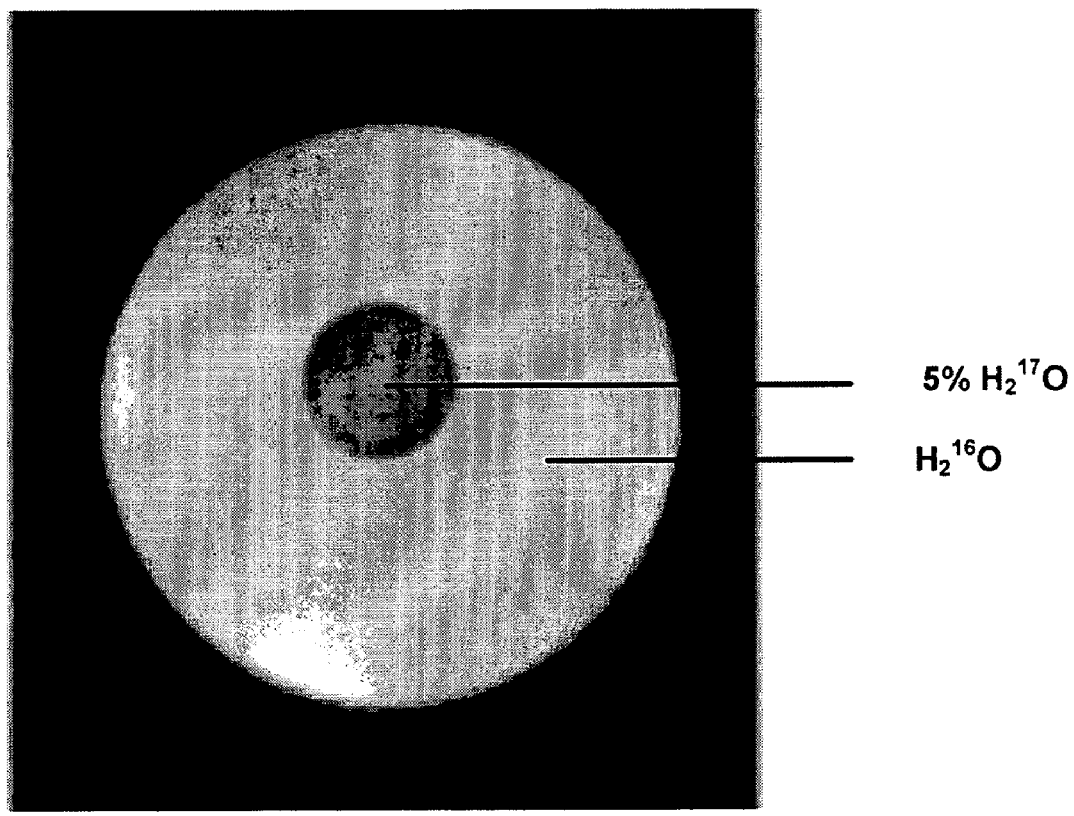
FIG. 3 is an exemplary MRI image illustrating microimaging of $H_2^{17}O$.

FIG. 3 is an exemplary MRI image 15 illustrating micro-imaging of $H_2^{17}O$. The MRI image illustrates a difference in image contrast between $^{16}$O and $^{17}$O molecules.

Accordingly, in the present invention, a GPC molecule is synthesized in which the standard $^{16}$O atoms are substituted with $^{17}$O atoms. GPC molecules selectively bind to the β-turn within an Aβ peptide, providing a specific marker for this precursor to the development of Aβ peptide aggregates in Alzheimer's disease. Notably, GPC contains six original $^{16}$O atoms that could be replaced with $^{17}$O. If all six original $^{16}$O of GPC are replaced with $^{17}$O, the strength of the paramagnetic signal is greatly increased. However, not all of the original $^{16}$O atoms need to be replaced to practice the invention.

Figure 4:
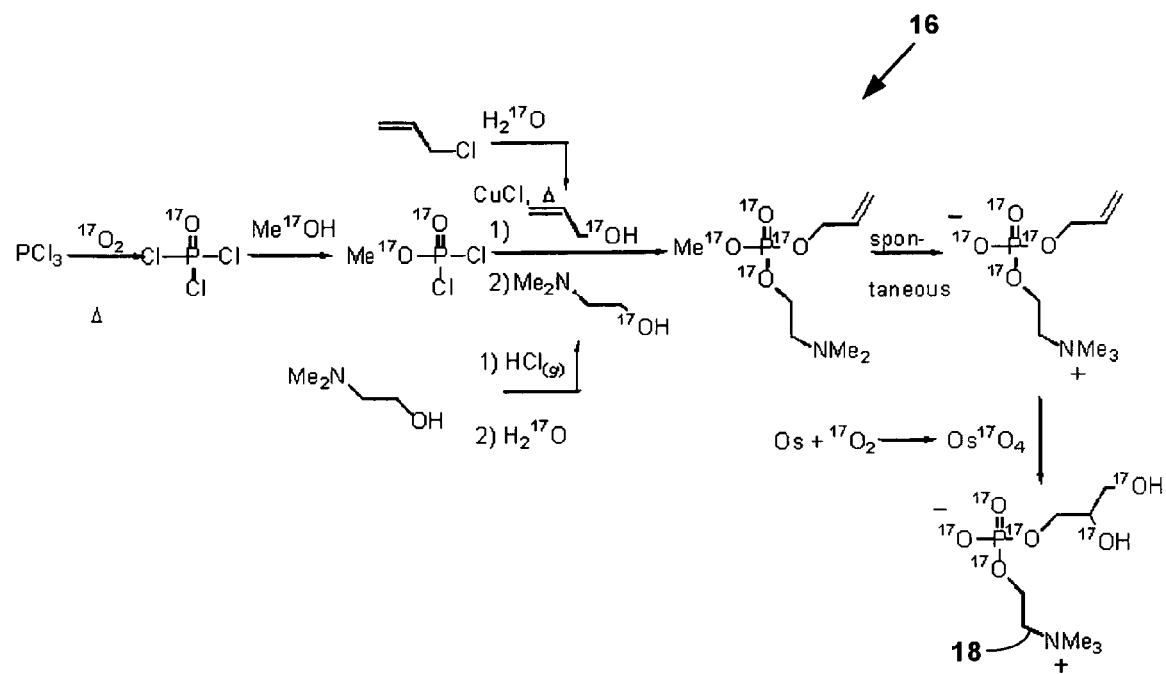
FIG. 4 is a block diagram illustrating details of a chemical reaction used to create a synthesized GPC molecule.

FIG. 4 is a block diagram 16 illustrating details of a chemical reaction used to create a synthesized GPC molecule 18. In one embodiment of the invention each of the six $^{16}$O atoms on an original GPC molecule 14 are replaced with six $^{17}$O atoms to create a synthesized GPC molecule 18 (original GPC molecule 14, 14' 14" and synthesized GPC molecule 18 are shown in two different chemical formula structures that are equivalent except the original GPC molecule 14 includes $^{16}$O atoms and the synthesized GPC molecule includes $^{17}$O atoms). The synthesis of the synthesized GPC molecule 18 is based on the partial literature precedent established by Lacey et al. (J. Org. Chem. 1983; 48: 5214-5521) and Wassermann (D R Colloq. Int. Isot. Oxygene 1975; Meeting Date 1972: 95-98), the contents of both of which are incorporated herein by reference. In FIG. 4, the $^{17}$O-labelled starting materials (e.g., $^{17}O_2$, $H_2^{17}O$, and $CH_3^{17}OH$) are commercially available from many sources.

In another embodiment of the invention, GPC molecules can be synthesized using $^{16}$O (naturally abundant isotope) starting materials to create a synthesized GPC molecule via a similar chemical reaction.

However, the present invention is not limited to such an embodiment and less than all six $^{16}$O atoms on an original GPC molecule are replaced with six $^{17}$O atoms to create other forms of synthesized GPC molecules. In addition, other chemical reactions and other chemical compounds and techniques can also be used to practice the invention and the invention is not limited to the chemical reaction, compounds or techniques described herein.

In the chemical reaction of FIG. 4, phosphorous trichloride is converted to [$^{17}$O]phosphoryl chloride, for example by spark-ignited combustion of phosphorous trichloride in a $^{17}O_2$ atmosphere. The [$^{17}$O]phosphoryl chloride is then converted to [$^{17}O_2$]phosphorodichloridic acid methyl ester by methanolysis with [$^{17}$O]methanol. The methyl ester is converted to the phosphate diester by successive displacement of the chlorines by [$^{17}$O]allyl alcohol (which may be prepared by hydrolysis of allyl chloride with $H_2^{17}O$) and [$^{17}$O]dimethylethanolamine (which may be prepared by chlorination of nomoisotopic dimethylethanolamine with HCl gas and hydrolysis of the resulting dimethylaminoethyl chloride with $H_2^{17}O$).

The resulting triester is known to isomerize readily and spontaneously to allyl choline phosphate. The double bond is then dihydroxylated with [$^{17}O_4$]osmium tetroxide (which may be prepared by passing $^{17}O_2$ gas over finely slivered metallic osmium) to yield racemic [$^{17}O_6$]GPC. The individual enantiomers of [$^{17}O_6$]GPC (e.g., the natural 2R and the unnatural 2S forms) can be individually prepared by use of the SHARPLESS asymmetric dihydroxylation method (e.g., from U.S. Pat. No. 4,965,364, which is hereby incorporated herein by reference) in the final dihydroxylation step. However, the present invention is not limited to such an embodiment and the other methods and techniques can also be used to create the synthesized GPC molecules.

As stated above, the synthesized [$^{17}O_6$] GPC molecule 18 is useful in MRI imaging of GPC binding to β-turns within an Aβ peptide. Therefore, this synthesized GPC molecule 18 can be used for the non-invasive measurement of Aβ peptides containing β-turns in human and animal subjects. Such synthesized GPC molecules 18 are capable of efficiently crossing the blood-brain barrier and subsequently specifically binding to Aβ peptides containing β-turns.

In one embodiment of the invention, the synthesized GPC molecule 18 is compound that can be ingested in solid form (e.g., pill form) or liquid form (e.g., used via an IV) for human or animal subjects. The synthesized GPC molecule 18 does not require any further processing and does not have any known negative side effects. The original GPC molecule is a naturally occurring compound in human and animal subjects.

In another embodiment of the invention, the synthesized GPC molecule 14 is combined with other pharmaceutically acceptable compounds know in the art to form a composition. Such pharmaceutically acceptable compounds include solids and liquids.

Returning to the chemical reaction illustrated in FIG. 4, additional substitutions of replacement atoms for original atoms within the GPC molecule are within the scope of the present invention. Such substitutions may include substitution of fluorine ($^{19}F$ for MRI, $^{18}F$ for PET) for the hydrogens on the methyl group on the GPC molecule and, alternatively or in combination, phosphonyl derivatives of the GPC molecule. In the phosphonyl derivatives, at least one of the oxygen atoms on the phosphoryl group of GPC are replaced with a carbon atom. Such derivatives of GPC may contain the added benefit of not being a substrate for the physiological enzymes that usually degrade GPC. Thus, the half life of these GPC derivatives would be increased in vivo, increasing their effectiveness in imaging applications.

Additional presently-preferred compositions of the present invention include GPC molecules in which normal atoms have been substituted with radioactive isotopes that are capable of emitting positrons as they decay. These embodiments of the present invention would preferably have a short period of instability during which they would emit positrons, and would thus pose a limited medical risk to subjects. Such molecules would be useful in PET imaging of GPC binding to β-turns within an Aβ peptide molecule. Such substitutions may include $^{15}O$ for $^{16}O$, $^{13}N$ for $^{14}N$, and $^{11}C$ for $^{12}C$. A $^{18}F$ atom may be substituted for hydrogens on methyl groups of the GPC molecule without any loss of binding specificity. Accordingly, such substitutions are within the scope of the present invention.

The synthetic reaction scheme illustrated in FIG. 4 may also be used to synthesize several of these radioactive derivatives of GPC. Where deviations from this synthetic reaction scheme are required, one of skill in the art would be well aware of how to make such modifications. As a result, the chemical reactions for these modifications are not illustrated.

Diagnosing Alzheimer Disease with GPC

Figure 5:
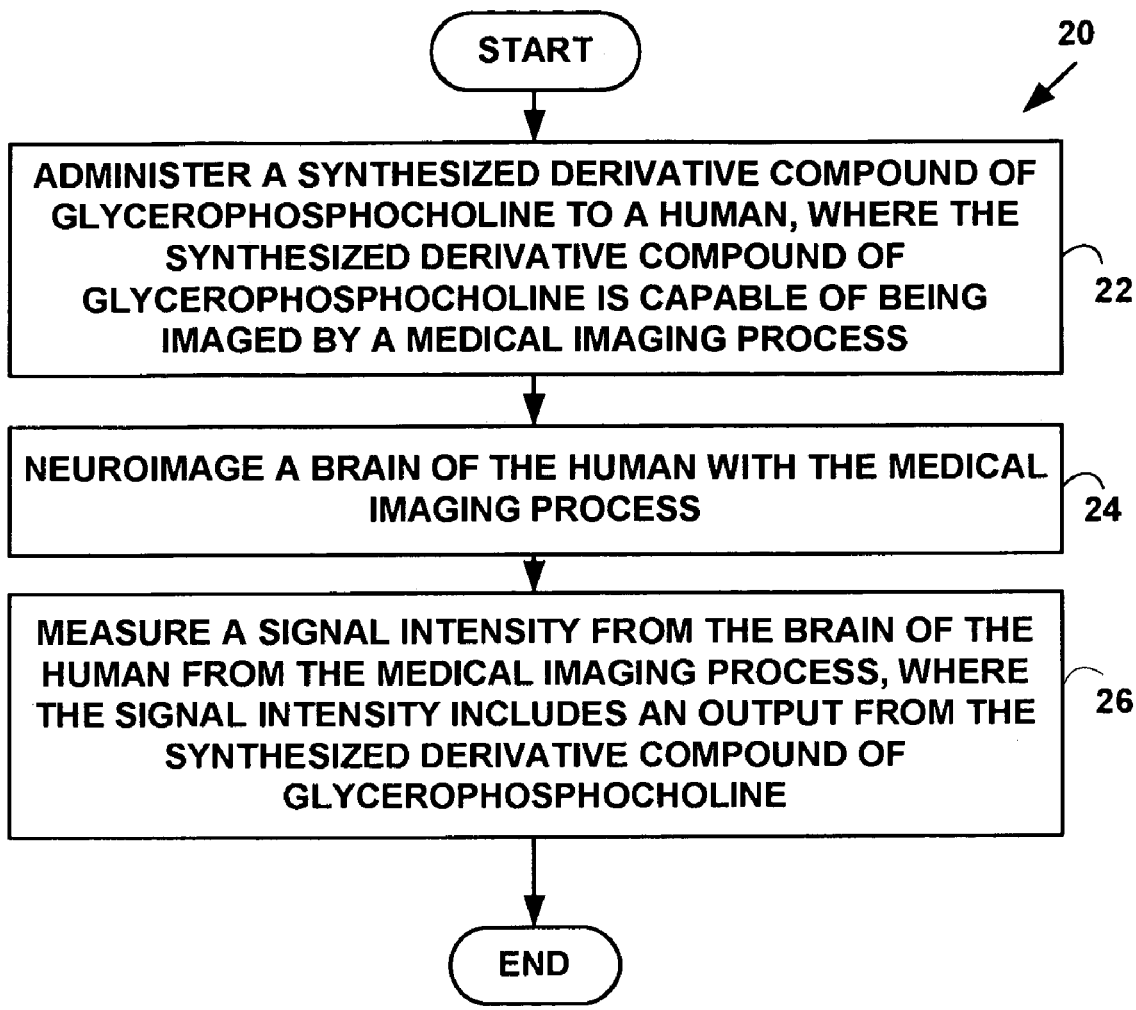
FIG. 5 is a flow diagram illustrating a method for diagnosing Alzheimer's disease in a human.

FIG. 5 is a flow diagram illustrating a Method 20 for diagnosing Alzheimer's disease in a human. At Step 22 a synthesized derivative compound of GPC is administered to a human. The synthesized derivative compound of GPC is capable of being imaged by a medical imaging process. At Step 24, a brain of the human is imaged with the medical imaging process. At Step 26, a signal intensity from the brain of the human is measured with the medical imaging process. The signal intensity includes an output from the synthesized derivative compound of GPC.

Method 20 is illustrated with an exemplary embodiment. However, the present invention is not limited to this exemplary embodiment and other embodiments can also be used to practice the invention.

At Step 22 a synthesized derivative compound of GPC is administered to a human. The synthesized derivative compound of GPC is capable of being imaged by a medical imaging process. In one embodiment, the synthesized derivative compound of GPC includes replacing original $^{16}O$ atoms of original GPC molecules with $^{17}O$ atoms via the chemical reaction illustrated in FIG. 4. In another embodiment, the synthesized derivative compound of GPC includes replacing original $^{16}O$ atoms with $^{15}O$ atoms, original $^{14}N$ atoms with $^{13}N$ atoms, or replacing original $^{12}C$ atoms with $^{11}C$ atoms. In another embodiment of the invention, hydrogens on the methyl moiety of the naturally occurring or a synthesized derivative compound of GPC are replaced with $^{18}F$ atoms.

The replacement $^{15}O$, $^{13}N$, $^{11}C$, and $^{18}F$ atoms are radioactive isotopes that are capable of emitting positrons as they decay.

Returning to FIG. 5, at Step 24, a brain of the human is imaged with the medical imaging process. The medical imaging process includes, but not limited to, MRI or PET or other medical imaging processes.

At Step 26, a signal intensity from the brain of the human is measured with the medical imaging process. The signal intensity includes an output from the synthesized derivative compound of GPC. Step 26 includes measuring a signal intensity of an output from a binding of plural molecules of the synthesized derivative compound of GPC to β-turns within Aβ peptide within the human brain.

Figure 6:
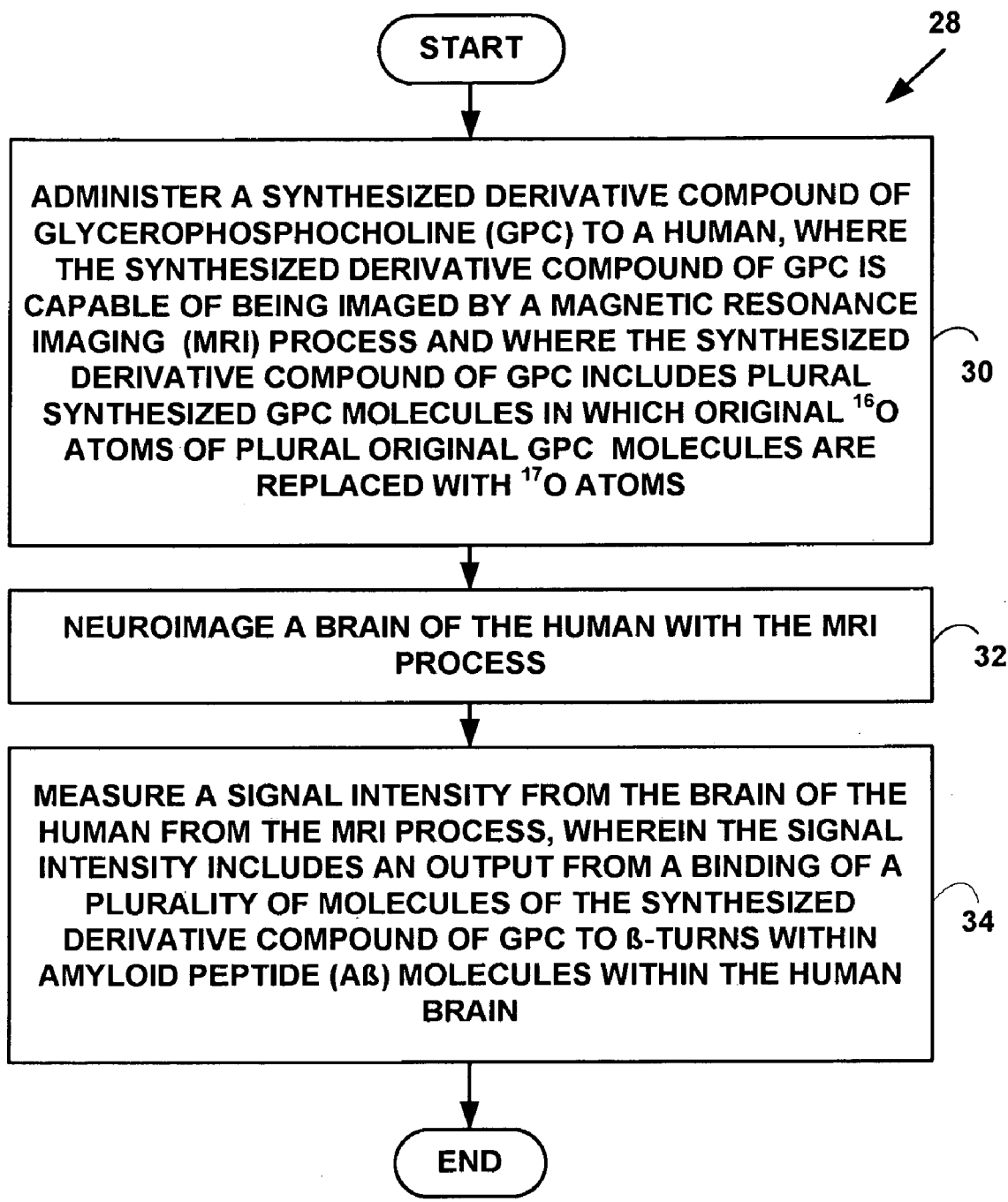
FIG. 6 is a flow diagram illustrating a method for diagnosing Alzheimer's disease in a human.

FIG. 6 is a flow diagram illustrating a Method 28 for diagnosing Alzheimer's disease in a human. At Step 30, a synthesized derivative compound of GPC is administered to a human. The synthesized derivative compound of GPC is capable of being imaged by a MRI process. The synthesized derivative compound of GPC includes plural synthesized GPC molecules in which original $^{16}O$ atoms of plural original GPC molecules are replaced with $^{17}O$ atoms. At Step 32, a brain of the human is imaged with the MRI process. At Step 34, a signal intensity from the brain of the human is measured from the MRI process. The signal intensity includes an output from a binding of plural molecules of the synthesized derivative compound of GPC to β-turns within Aβ peptide within the human brain.

Figure 7:
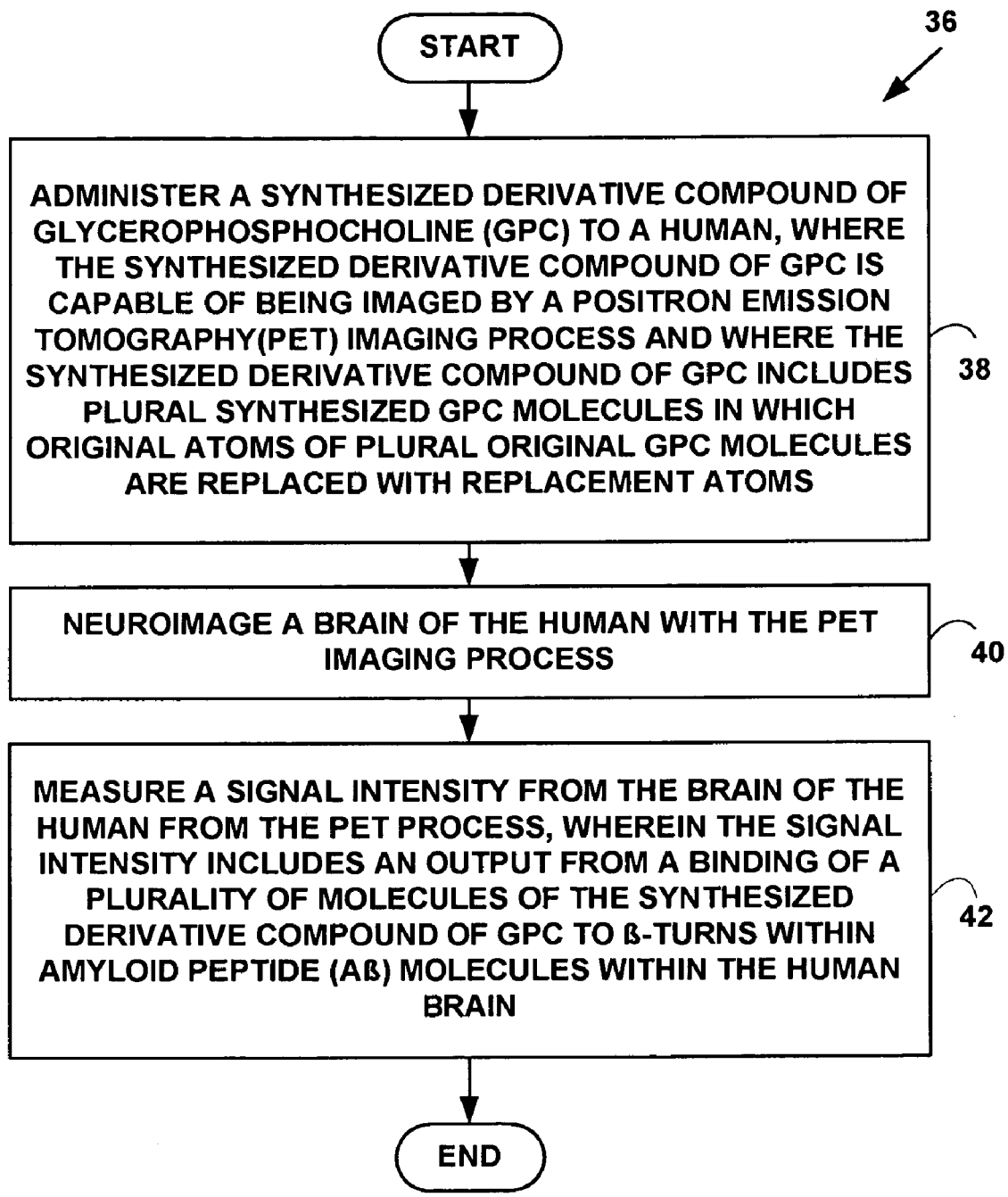
FIG. 7 is a flow diagram illustrating a method for diagnosing Alzheimer's disease in a human.

FIG. 7 is a flow diagram illustrating a Method 34 for diagnosing Alzheimer's disease in a human. At Step 36, a synthesized derivative compound of GPC is administered to a human. The synthesized derivative compound of GPC is capable of being imaged by a PET imaging process. The synthesized derivative compound of GPC includes plural synthesized GPC molecules in which original atoms of plural original GPC molecules are replaced with replacement atoms. At Step 38, a brain of the human is imaged with the PET imaging process. At Step 40, a signal intensity from the brain of the human is measured from the PET process. The signal intensity includes an output from a binding of plural molecules of the synthesized derivative compound of GPC to β-turns within Aβ peptide within the human brain.

In one embodiment of the invention, replacement atoms include, but are not limited to, replacement atoms in which $^{15}O$ atoms are used to replace $^{16}O$ atoms, $^{13}N$ atoms are used to replace $^{14}N$ atoms, $^{11}C$ atoms are used to replace $^{12}C$ atoms, or hydrogens on the methyl moieties are replaced with $^{18}F$ atoms to be used for PET imaging.

Diagnosing Parkinson's Disease with GPC

Parkinson's disease is disease of the nervous system caused by degeneration of a part of the brain called the basal ganglia, and by low production of the neurotransmitter dopamine. Symptoms include muscle rigidity, tremors, and slow voluntary movement. Dementia occurs in 15%-20% of cases. There has been some recent research into studying β turns in Aβ peptides for diagnosing other diseases of the brain. See for example, Ulmer et al., *J. Biol. Chem.* 2005; 280: 9595.

Individuals with Parkinson's Disease develop Lewy bodies and α-synuclein cytoplasmic inclusions in cortical neurons. Lewy bodies are characteristic intracellular proteinaceous inclusions that are formed in the brains of individuals with Parkinson's disease. The Lewy bodies include high levels of the protein alpha-synuclein.

As is known in the art, alpha-synuclein is one of a family of structurally related proteins that are prominently expressed in the central nervous system of a human subject. Aggregated alpha-synuclein proteins form brain lesions that are hallmarks of some neurodegenerative diseases such as Alzheimer's disease, Parkinson's disease, etc.

Figure 8:
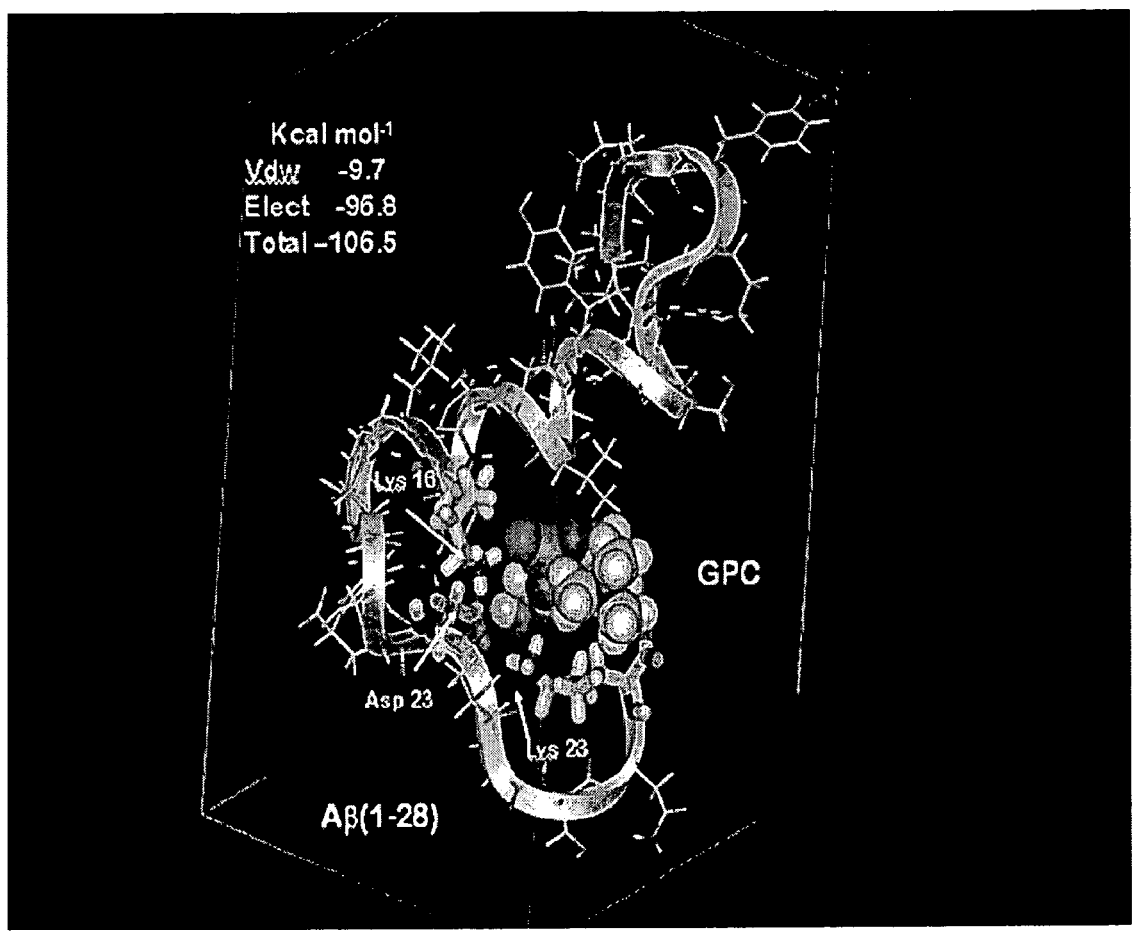
FIG. 8 is a block diagram illustrating Molecular modeling of GPC binding to Aβ(1-28)

FIG. 8 is a block diagram 42 illustrating molecular modeling of GPC binding to Aβ(1-28).

Figure 9:
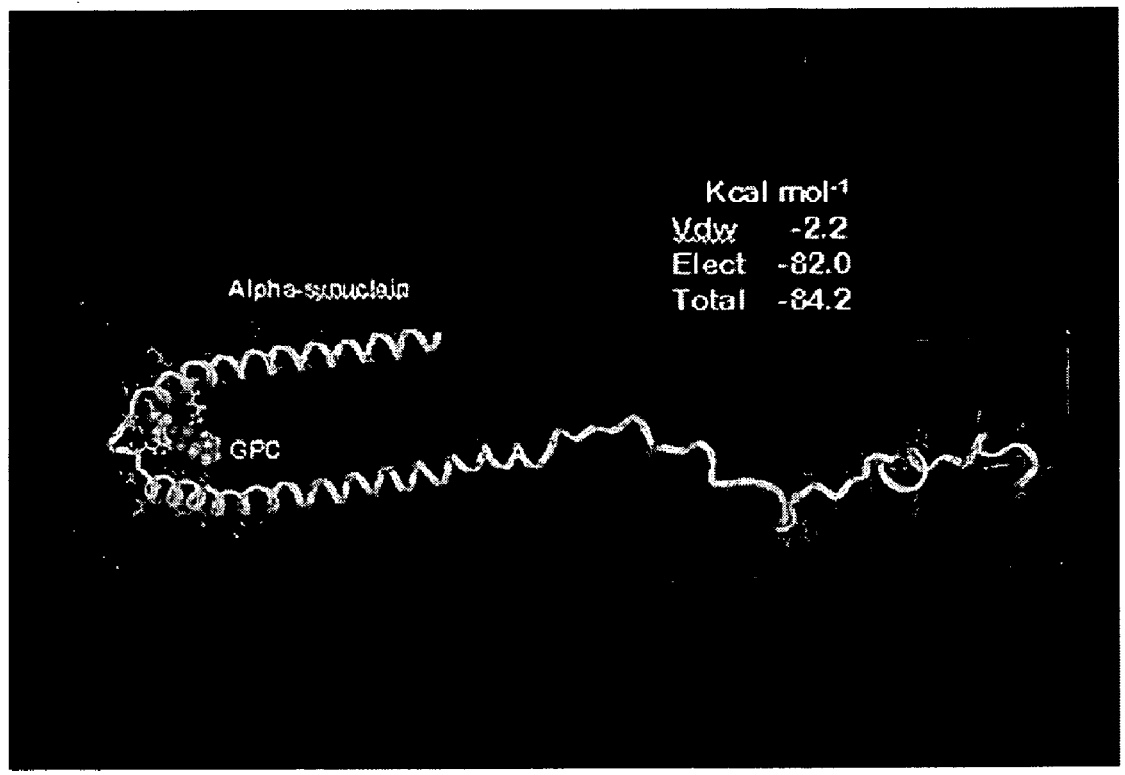
FIG. 9 is a block diagram illustrating molecular modeling of GPC binding to human micelle-bound alpha-synuclein.

FIG. 9 is a block diagram 44 illustrating molecular modeling of GPC binding to human micelle-bound alpha-synuclein. The alpha-synuclein or α-synuclein structure was obtained from an NMR minimized average structure and protein data bank structure 1XQ8 (See e.g., Ulmer et al., *J. Biol. Chem.* 2005; 280: 9595).

Figure 10:
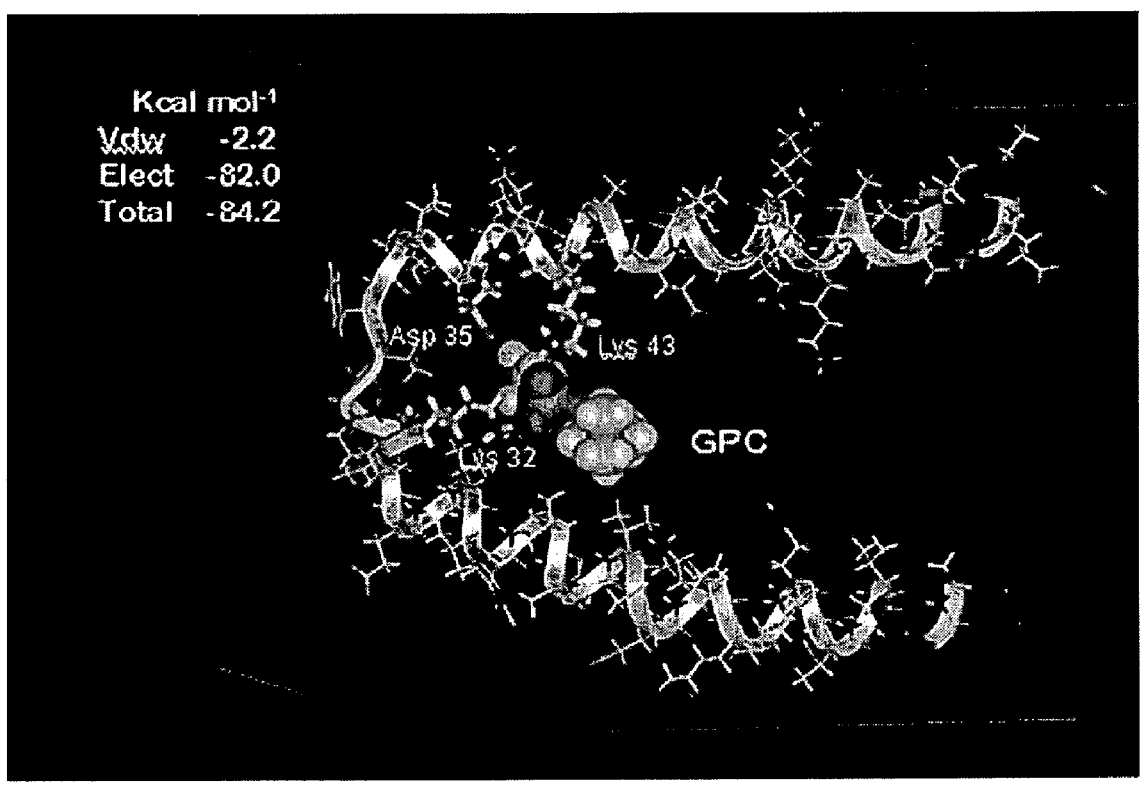
FIG. 10 is a block diagram additional details of molecular modeling of GPC binding to human micelle-bound alpha-synuclein.

FIG. 10 is a block diagram 46 additional details of molecular modeling of GPC binding to human micelle-bound alpha-synuclein. The alpha-synuclein structure was obtained from an NMR minimized average structure and protein data bank structure 1XQ8.

Previous studies by the inventors of this patent application have demonstrated GPC 14 (FIG. 2) stabilizes a β-turn in Aβ peptide (FIG. 8) promoting β-sheet formation leading to β-sheet oligomerization culminating in extracellular amyloid deposits (FIG. 1) in brains of human Alzheimer's disease (AD) patients. Using this information, isotope derivatives of GPC 18, etc. as discussed above were used for MRI and PET imaging of these key chemical events as a molecular biomarker for Alzheimer's disease in which this process occurs.

More recent studies by the inventors of this patent application now demonstrate GPC stabilizes a hairpin turn linkage between two α-helices in α-synuclein protein (FIGS. 9 and 10) leading to β-sheet formation and aggregation of α-synuclein into intracellular deposits known as Lewy bodies which occur in Parkinson's disease. Isotope derivatives of original GPC 14 are created as was discussed above for Alzheimer's disease are now used for MRI and PET imaging of this key molecule (i.e., α-synuclein) in the detection and diagnosis Parkinson's disease. The detection by medical imaging processes occurs in the basal ganglia and neurocortex of the human brain.

As was discussed above, one of the atomic moieties of normal GPC 14 is used to create derivative compounds of GPC 18, etc. The derivative compound of GPC includes, one or more substitutions in various combinations of a non-radioactive ($^{19}F$, $^{16}O$), paramagnetic ($^{17}O$), or radioactive ($^{15}O$, $^{13}N$, $^{11}C$, $^{18}F$) isotope of a same or physiochemically related moiety in GPC 14. The modified GPC molecule is used with MRI and PET imaging to detect bindings of α-synuclein to detect and diagnosis Parkinson's disease.

For example replacing $^{16}O$ atoms with $^{17}O$ atoms, hydrogen atoms on methyl moieties with $^{19}F$ atoms, replacing hydrogen atoms on methyl moieties with $^{18}F$ atoms and/or replacing at least one oxygen atom in a phosphoryl group with a $CH_2$ group for MRI imaging.

For example, hydrogen atoms on methyl moieties are replaced with $^{18}F$ atoms or $^{19}F$ and with at least one modification selected from a group consisting of replacing $^{17}O$ atoms with $^{15}O$ atoms, $^{17}O$ atoms with $^{16}O$ atoms, replacing $^{14}N$ atoms with $^{13}N$ atoms and/or replacing $^{12}C$ atoms with $^{11}C$ atoms for PET imaging.

In another embodiment, one or more of the replacement described for PET imaging are also used for MRI imaging and visa versa. However, the present invention is not limited to these replacements and more, fewer or other replacements can also be made in other combinations to practice the invention to detect and diagnosis Parkinson's disease.

Figure 11:
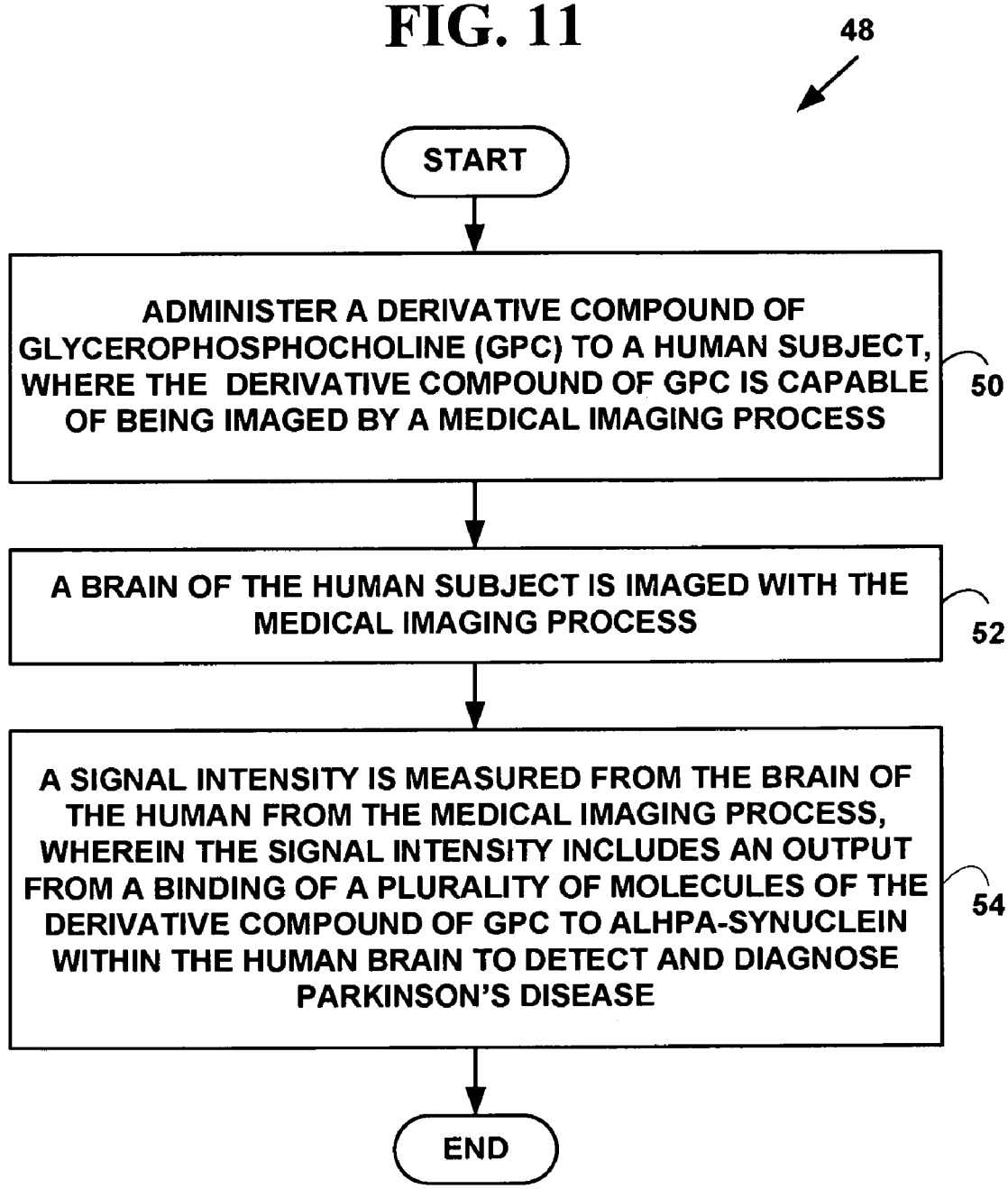
FIG. 11 is a flow diagram illustrating a method for detecting and diagnosing Parkinson's disease in a human using a medical imaging process.

FIG. 11 is a flow diagram illustrating a Method 48 for detecting and diagnosing Parkinson's disease in a human. At Step 50, a derivative compound of GPC is administered to a human subject. The derivative compound of GPC is capable of being imaged by a medical imaging process. The derivative compound of GPC includes any of the combinations of substations discussed above. At Step 52, a brain of the human subject is imaged with the medical imaging process. At Step 54, a signal intensity from the brain of the human is measured from the medical imaging process. The signal intensity includes an output from a binding of plural molecules of the derivative compound of GPC to α-synuclein within the human brain to detect and diagnosis Parkinson's disease.

Figure 12:
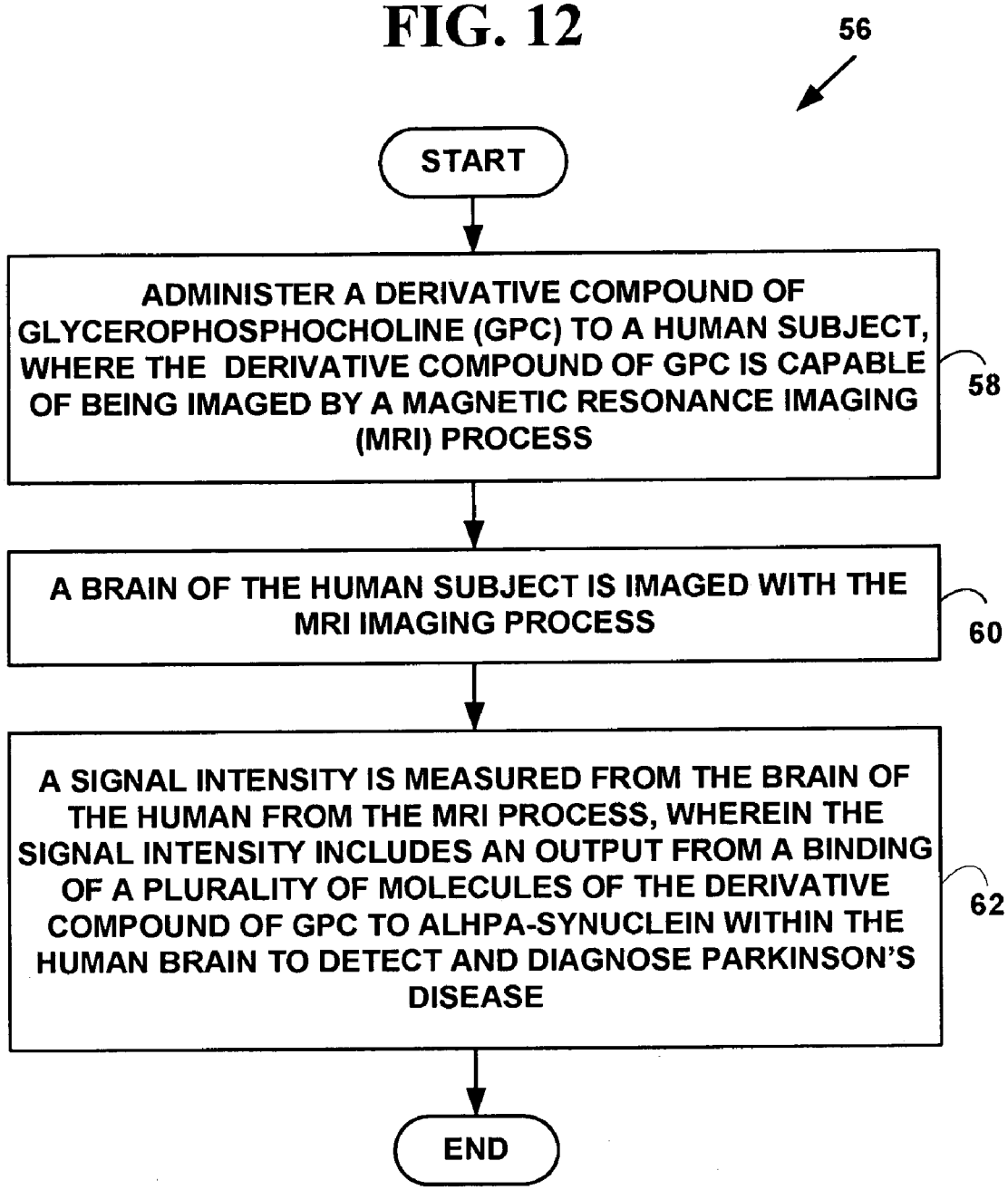
FIG. 12 is a flow diagram illustrating a method for detecting and diagnosing Parkinson's disease in a human using MRI imaging.

FIG. 12 is a flow diagram illustrating a Method 56 for detecting and diagnosing Parkinson's disease in a human. At Step 58, a derivative compound of GPC is administered to a human subject. The derivative compound of GPC is capable of being imaged by a MRI process. The derivative compound of GPC includes any of the combinations of substations discussed above. At Step 60, a brain of the human subject is imaged with the MRI process. At Step 62, a signal intensity from the brain of the human is measured from the MRI process. The signal intensity includes an output from a binding of plural molecules of the derivative compound of GPC to α-synuclein within the human brain to detect and diagnose Parkinson's disease.

Figure 13:
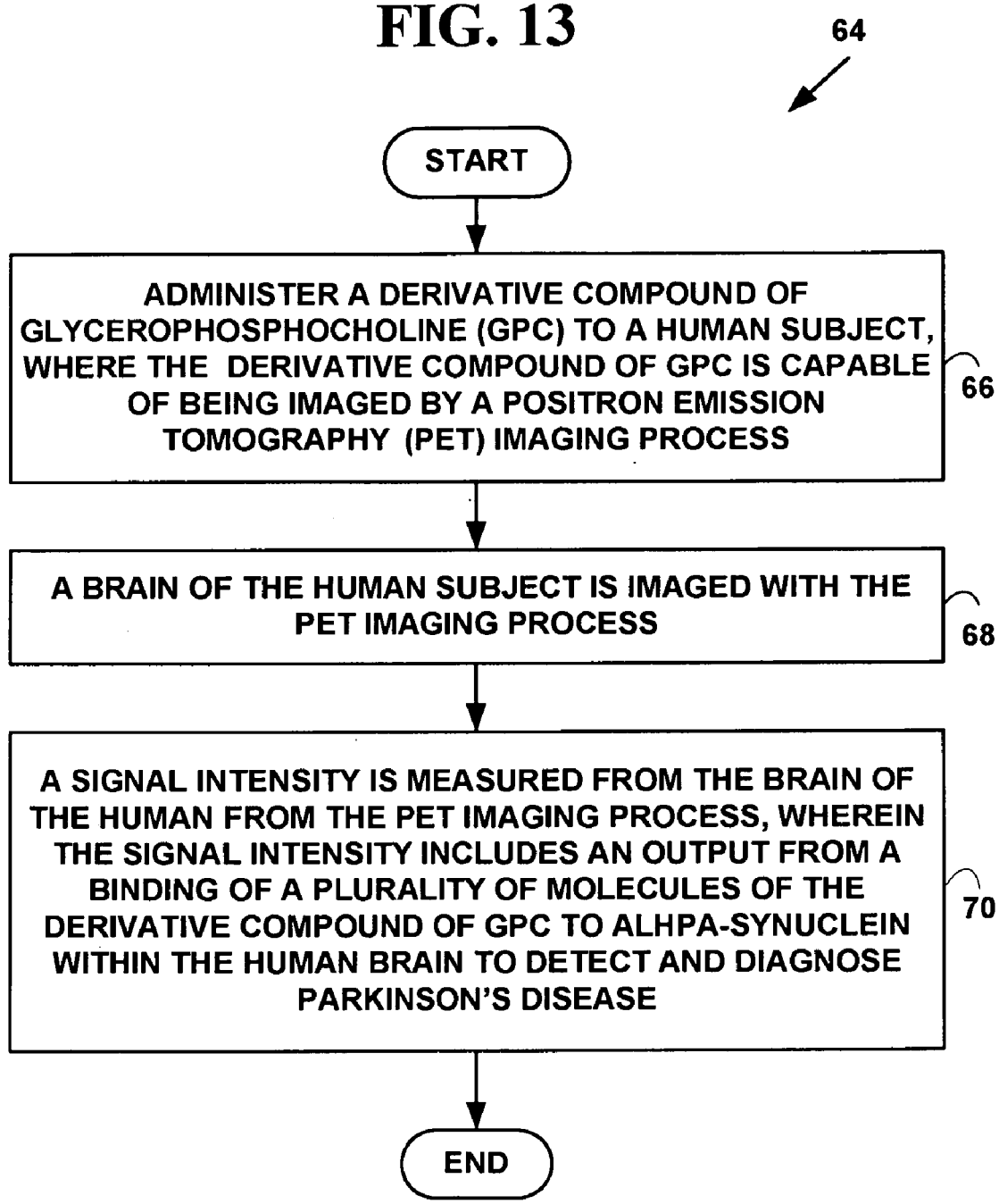
FIG. 13 is a flow diagram illustrating a method for detecting and diagnosing Parkinson's disease in a human using PET imaging.

FIG. 13 is a flow diagram illustrating a Method 64 for detecting and diagnosing Parkinson's disease in a human. At Step 66, a derivative compound of GPC is administered to a human subject. The derivative compound of GPC is capable of being imaged by a PET process. The derivative compound of GPC includes any of the combinations of substations discussed above. At Step 68, a brain of the human subject is imaged with the PET process. At Step 70, a signal intensity from the brain of the human is measured from the PET process. The signal intensity includes an output from a binding of plural molecules of the derivative compound of GPC to α-synuclein within the human brain to detect and diagnose Parkinson's disease.

Figure 14:
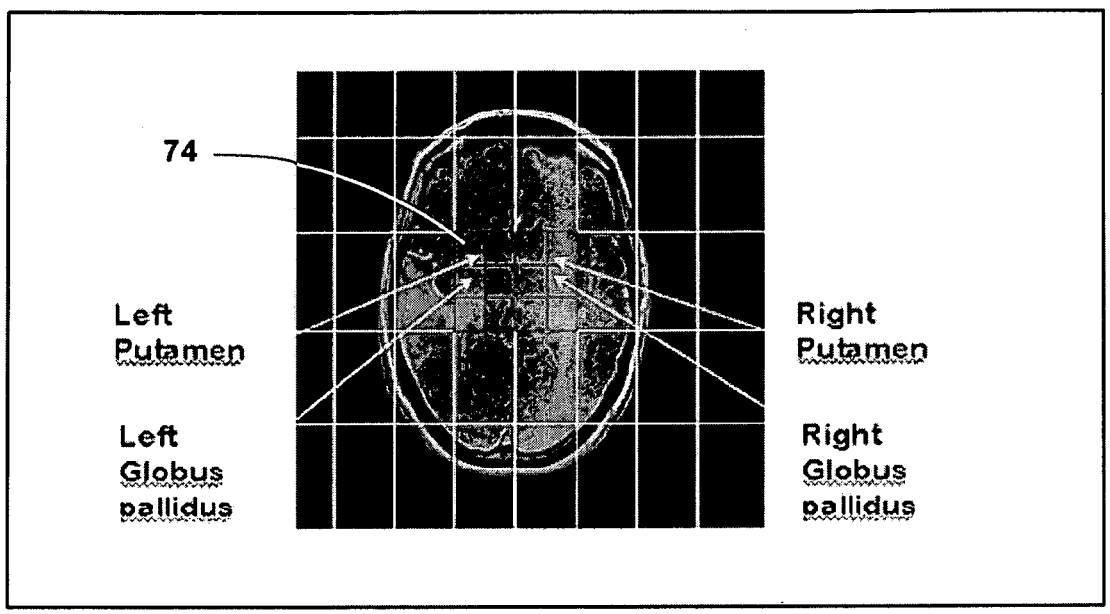
FIG. 14 is a block diagram illustrating a scan of human brain illustrating response of a derivative compound of GPC binding to human micelle-bound alpha-synuclein for detecting and diagnosing Parkinson's disease.

FIG. 14 is a block diagram 72 illustrating a medical imaging scan of a human brain illustrating a response 74 of a derivative compound of GPC binding to human micelle-bound α-synuclein for detecting and diagnosing Parkinson's disease.

Derivative glycerophosphocholine (GPC) compounds are used as a detection and diagnostic aid to measure progression of Parkinson's disease by detecting GPC binding to α-synuclein. Derivative compounds including non-radioactive, paramagnetic, and radioactive derivatives of GPC are presented. These compounds possess similar binding properties to original GPC molecules and are useful in medical magnetic resonance imaging (MRI) and/or positron emission tomography (PET) applications. By employing these radiological techniques in the detection, diagnosis and assessment of the progression of Parkinson's disease may be achieved.

It should be understood that the programs, processes, methods and system described herein are not related or limited to any particular type of chemical or biological systems unless indicated otherwise. Various combinations of general purpose, specialized or equivalent chemical or biological components may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more, fewer or equivalent elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

We claim:

1. A method for detecting and diagnosing Parkinson's disease in a human, comprising administering to a patient a synthetic glycerophosphocholine (GPC) compound based upon the following formula modified as set forth and consisting essentially of:

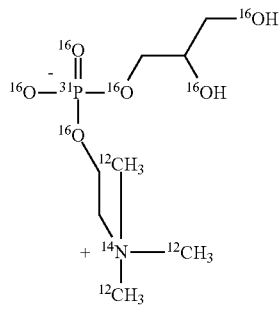

by replacing at least one hydrogen atom on at least one methyl moiety with $^{19}$F, or replacing at least one hydrogen atom on at least one methyl moiety with $^{18}$F, and imaging a brain of said patient with a medical imaging process by measuring a signal intensity from the brain of said patient via said medical imaging process, wherein said signal intensity includes an output from a binding of plural molecules of said synthetic GPC compound to α-synuclein within the human brain to detect and diagnose Parkinson's disease.

2. The method of claim 1 wherein the medical imaging process is selected from the group consisting of Magnetic Resonance Imaging (MRI) and positron emission tomography (PET).

* * * * *